United States Patent
Moeckel et al.

(10) Patent No.: US 7,101,690 B2
(45) Date of Patent: Sep. 5, 2006

(54) ATTENUATED CCPA1 MODIFIED BACTERIAL CELL AND ITS USE FOR THE PREPARATION OF L-AMINO ACIDS

(75) Inventors: Bettina Moeckel, Duesseldorf (DE); Caroline Kreutzer, Melle (DE)

(73) Assignee: Degussa AG, Duesseldorf (DE)

( * ) Notice: Subject to any disclaimer, the term of this patent is extended or adjusted under 35 U.S.C. 154(b) by 69 days.

(21) Appl. No.: 10/895,849

(22) Filed: Jul. 22, 2004

(65) Prior Publication Data

US 2005/0032179 A1 Feb. 10, 2005

Related U.S. Application Data

(63) Continuation of application No. 09/938,540, filed on Aug. 27, 2001, now Pat. No. 6,838,267.

(60) Provisional application No. 60/279,413, filed on Mar. 29, 2001.

(30) Foreign Application Priority Data

Aug. 26, 2000 (DE) ............... 100 42 054
Mar. 2, 2001 (DE) ............... 101 10 052

(51) Int. Cl.
*C12P 13/04* (2006.01)
*C12N 1/20* (2006.01)
*C12N 15/00* (2006.01)
*C07K 1/00* (2006.01)
*C07H 21/02* (2006.01)

(52) U.S. Cl. .............. 435/106; 435/41; 435/69.1; 435/252.32; 435/320.1; 530/350; 536/23.1

(58) Field of Classification Search ........... 435/41, 435/69.1, 106, 252.3, 320.1, 252.32; 530/350; 536/23.1
See application file for complete search history.

(56) References Cited

U.S. PATENT DOCUMENTS 6,689,586 B1   2/2004   Moeckel et al.

FOREIGN PATENT DOCUMENTS

EP        1 108 790       6/2001

OTHER PUBLICATIONS

U.S. Appl. No. 10/724,827, filed Dec. 2, 2003, Moeckel, et al.
U.S. Appl. No. 10/895,849, filed Jul. 22, 2004, Moeckel, et al.
V. Monedero, et al., Journal of Bacteriology, vol. 179, No. 21, XP-002916657, pp. 6657-6664, "Catabolite Repression in *Lactobacillus casei* TCC 393 is mediated by CcpA", Nov. 1997.
O. Egeter, et al., Molecular Microbiology, vol. 21, No. 4, XP-002916663, pp. 739-749, "Catabolite Repression Mediated by the Catabolite Control Protein CcpA in *Staphylococcus xylosus*", 1996.
K. J. Seeger, et al., Database EMBL online, AN Q9RD12, XP-002199084, pp. 1-2, "Probable LacI-Family Transcriptional Regulator", Jan. 2000.
C. Jourlin-Castelli, et al., Journal of Molecular Biology, vol. 295, XP-002199100, pp. 865-878, "CcpC, A Novel Regulator of the LysR Family Required for Glucose Repression of the citB Gene in *Bacillus subtilis*", Jan. 2000.
Attwood et al., Which craft is best in bioinformatics? Comput. Chem. 2001, vol. 25(4), pp. 329-339.
Ponting, C.P. Issues in predicting protein function from sequence. Brief. Bioinform. Mar. 2001, vol. 2(1), pp. 19-29.
Chang et al. Accession AF260427. Jun. 5, 2000.
Sanchez et al. Accession AZ048854. Sep. 1, 2000.

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

The present invention provides isolated polynucleotides containing a polynucleotide sequence which is:
a) polynucleotide which is identical to the extent of at least 70% to a polynucleotide which codes for a polypeptide which comprises the amino acid sequence of SEQ ID No. 2, or
b) polynucleotide which codes for a polypeptide which comprises an amino acid sequence which is identical to the extent of at least 70% to the amino acid sequence of SEQ ID No. 2, or
c) polynucleotide which is complementary to the polynucleotides of a) or b), or
d) polynucleotide comprising at least 15 successive nucleotides of the polynucleotide sequence of a), b) or c), and a process for the fermentative preparation of L-amino acids using coryneform bacteria in which at least the ccpA1 gene is present in attenuated form, and the use of the polynucleotide sequences as hybridization probes.

15 Claims, 1 Drawing Sheet

Figure 1: Plasmid map of pCR2.1ccpA1int
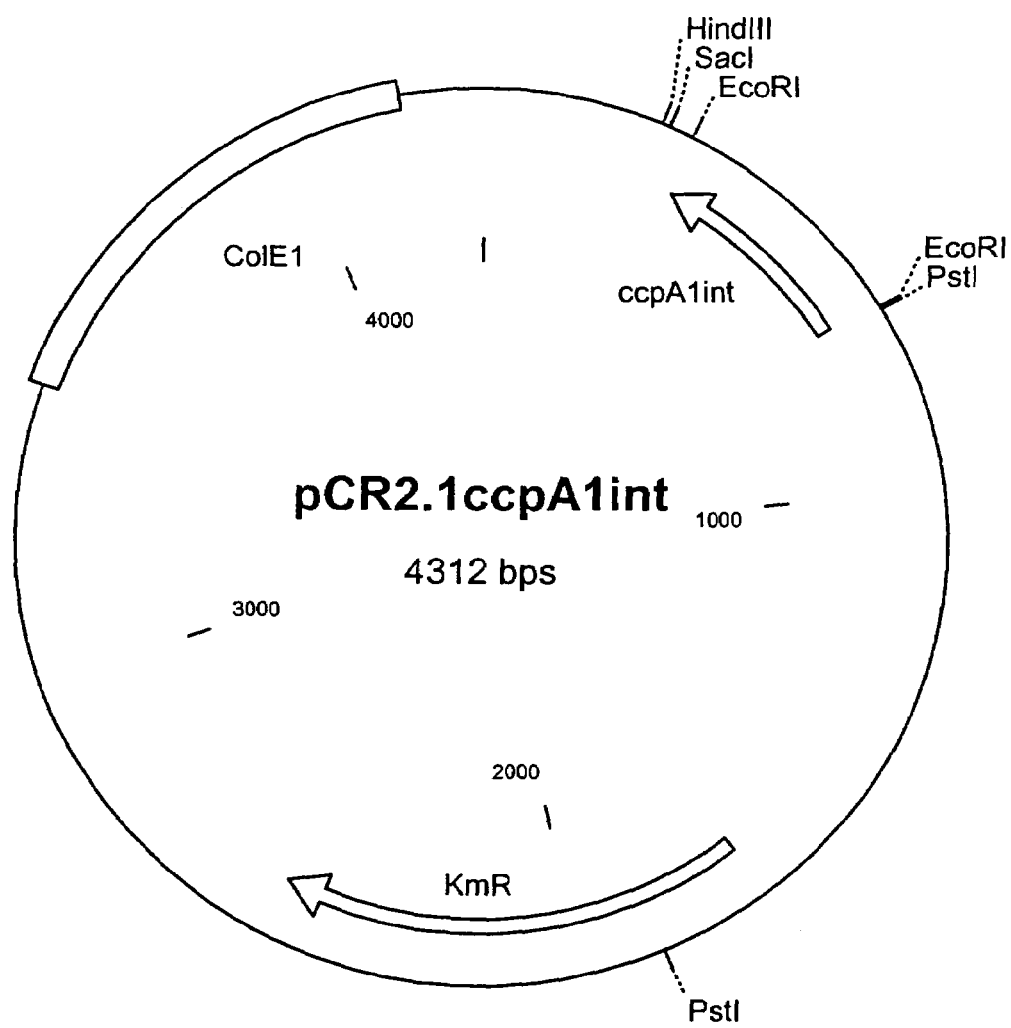

SEQUENCE LISTING

```
<160> NUMBER OF SEQ ID NOS: 4

<210> SEQ ID NO 1
<211> LENGTH: 1600
<212> TYPE: DNA
<213> ORGANISM: Corynebacterium glutamicum
<220> FEATURE:
<221> NAME/KEY: CDS
<222> LOCATION: (225)..(1388)
<223> OTHER INFORMATION: ccpA1-Gen

<400> SEQUENCE: 1
tgggttactg cccaggcaat gtttggatag tttttcgggc ttttatcaac agccaataac      60
agctctttcg cccattgagg tggagggct gttttttcat gccgtaagga aagtgcaagt     120
aagtgaaatc aagtggccta gatccattga cacttagact gtgacctagg cttgactttc     180
gtgggggagt ggggataagt tcatcttaaa cacaatgcaa tcga ttg cat tta cgt      236
                                                 Met His Leu Arg
                                                  1 tcc tta tcc cac aat agg ggt acc ttc cag aaa gtt ggt gag gag atg      284
Ser Leu Ser His Asn Arg Gly Thr Phe Gln Lys Val Gly Glu Glu Met
 5                  10                  15                  20
```

-continued

| | |
|---|---|
| gct tcc gaa acc tcc agc ccg aag aag cgg gcc acc acg ctc aaa gac<br>Ala Ser Glu Thr Ser Ser Pro Lys Lys Arg Ala Thr Thr Leu Lys Asp<br>                      25                            30                      35 | 332 |
| atc gcg caa gca aca cag ctt tca gtc agc acg gtg tcc cgg gca ttg<br>Ile Ala Gln Ala Thr Gln Leu Ser Val Ser Thr Val Ser Arg Ala Leu<br>                  40                        45                      50 | 380 |
| gcc aac aac gcg agc att ccg gaa tcc aca cgc atc cga gtg gtt gaa<br>Ala Asn Asn Ala Ser Ile Pro Glu Ser Thr Arg Ile Arg Val Val Glu<br>        55                        60                        65 | 428 |
| gcc gct caa aag ctg aac tac cgt ccc aat gcc caa gct cgt gca ttg<br>Ala Ala Gln Lys Leu Asn Tyr Arg Pro Asn Ala Gln Ala Arg Ala Leu<br>70                            75                        80 | 476 |
| cgg aag tcg agg aca gac acc atc ggt gtc atc att cca aac att gag<br>Arg Lys Ser Arg Thr Asp Thr Ile Gly Val Ile Ile Pro Asn Ile Glu<br>85                            90                        95                      100 | 524 |
| aac cca tat ttc tcc tca cta gca gca tcg att caa aaa gct gct cgt<br>Asn Pro Tyr Phe Ser Ser Leu Ala Ala Ser Ile Gln Lys Ala Ala Arg<br>                      105                      110                      115 | 572 |
| gaa gct ggg gtg tcc acc att ttg tcc aac tct gaa gaa aac cca gag<br>Glu Ala Gly Val Ser Thr Ile Leu Ser Asn Ser Glu Glu Asn Pro Glu<br>                120                      125                      130 | 620 |
| ctg ctt ggt cag act ttg gcg atc atg gat gac caa cgc ctc gat gga<br>Leu Leu Gly Gln Thr Leu Ala Ile Met Asp Asp Gln Arg Leu Asp Gly<br>                135                      140                      145 | 668 |
| atc atc gtg gtg cca cac att cag tca gag gaa caa gtc act gac ttg<br>Ile Ile Val Val Pro His Ile Gln Ser Glu Glu Gln Val Thr Asp Leu<br>150                            155                      160 | 716 |
| gtt aac agg gga gtg cca gta gtg ctg gca gac cgt agt ttt gtt aac<br>Val Asn Arg Gly Val Pro Val Val Leu Ala Asp Arg Ser Phe Val Asn<br>165                            170                      175                      180 | 764 |
| tcg tct att cct tcg gtt acc tca gat cca gtt ccg ggc atg act gaa<br>Ser Ser Ile Pro Ser Val Thr Ser Asp Pro Val Pro Gly Met Thr Glu<br>                      185                      190                      195 | 812 |
| gct gtg gac tta ctc ctg gca gct gac gtg caa ttg ggc tac ctt gcc<br>Ala Val Asp Leu Leu Leu Ala Ala Asp Val Gln Leu Gly Tyr Leu Ala<br>                200                      205                      210 | 860 |
| ggc ccg cag gat act tcc act ggt cag ctg cgt ctt aac act ttt gaa<br>Gly Pro Gln Asp Thr Ser Thr Gly Gln Leu Arg Leu Asn Thr Phe Glu<br>                215                      220                      225 | 908 |
| aga cta tgc gtg gac cgc ggc atc gtc gga gca tct gtc tat tac ggt<br>Arg Leu Cys Val Asp Arg Gly Ile Val Gly Ala Ser Val Tyr Tyr Gly<br>230                            235                      240 | 956 |
| ggc tac cgc caa gaa tct gga tat gac ggc atc aag gtg ctg atc aag<br>Gly Tyr Arg Gln Glu Ser Gly Tyr Asp Gly Ile Lys Val Leu Ile Lys<br>245                            250                      255                      260 | 1004 |
| cag gga gcc aat gcg att atc gct ggt gac tcc atg atg acc atc ggt<br>Gln Gly Ala Asn Ala Ile Ile Ala Gly Asp Ser Met Met Thr Ile Gly<br>                      265                      270                      275 | 1052 |
| gcg ttg ttg gct ctt cat gag atg aat ttg aag atc ggt gag gat gtg<br>Ala Leu Leu Ala Leu His Glu Met Asn Leu Lys Ile Gly Glu Asp Val<br>                280                      285                      290 | 1100 |
| cag ctc att ggg ttt gat aac aac cca att ttc cgg ctg cag aat cca<br>Gln Leu Ile Gly Phe Asp Asn Asn Pro Ile Phe Arg Leu Gln Asn Pro<br>                295                      300                      305 | 1148 |
| ccg ctg agc atc att gac cag cac gta caa gag atc ggt aag cgt gcg<br>Pro Leu Ser Ile Ile Asp Gln His Val Gln Glu Ile Gly Lys Arg Ala<br>310                            315                      320 | 1196 |
| ttt gag att ctg cag aag ctg atc aat ggg gac acc gcg caa aaa tct<br>Phe Glu Ile Leu Gln Lys Leu Ile Asn Gly Asp Thr Ala Gln Lys Ser | 1244 |

|  |  |  |  |  |  |  |  |  |  |  |  |  |  |  |  |
|---|---|---|---|---|---|---|---|---|---|---|---|---|---|---|---|
| | | 325 | | | | 330 | | | | 335 | | | | 340 | |
| gtg | gtg | att | cca | acg | cag | ctc | agc | atc | aat | gga | tca | acg | gcg | gtt | tcc | 1292
| Val | Val | Ile | Pro | Thr | Gln | Leu | Ser | Ile | Asn | Gly | Ser | Thr | Ala | Val | Ser |
| | | | | 345 | | | | 350 | | | | 355 | | | |
| caa | aag | gcg | gcc | gca | aag | gca | gca | aaa | gca | gcc | caa | aaa | gca | gcc | gcg | 1340
| Gln | Lys | Ala | Ala | Ala | Lys | Ala | Ala | Lys | Ala | Ala | Gln | Lys | Ala | Ala | Ala |
| | | 360 | | | | 365 | | | | 370 | | | | | |
| aaa | gcc | gca | cag | aac | acg | caa | cac | gag | gtg | agc | cta | gat | ggt | gaa | ctc | 1388
| Lys | Ala | Ala | Gln | Asn | Thr | Gln | His | Glu | Val | Ser | Leu | Asp | Gly | Glu | Leu |
| | 375 | | | | 380 | | | | 385 | | | | | | | tgaacaagcg cttcatcagc atgatcctgc accaatcctt cagttggata aagtctccaa    1448 gtcgtttggc ccagtcaacg tcattaatca agtgagcatc gatgttcgcc ctggcagggt    1508 gcttgcgctg ttgggtgaaa atggtgcggg taaatctacg ctgatcaaga tgatgtcggg    1568 tgtgtatcag cctgatggcg ggcagatttt gg    1600

<210> SEQ ID NO 2
<211> LENGTH: 388
<212> TYPE: PRT
<213> ORGANISM: Corynebacterium glutamicum

<400> SEQUENCE: 2

Met His Leu Arg Ser Leu Ser His Asn Arg Gly Thr Phe Gln Lys Val
 1               5                  10                  15

Gly Glu Glu Met Ala Ser Glu Thr Ser Ser Pro Lys Lys Arg Ala Thr
            20                  25                  30

Thr Leu Lys Asp Ile Ala Gln Ala Thr Gln Leu Ser Val Ser Thr Val
        35                  40                  45

Ser Arg Ala Leu Ala Asn Asn Ala Ser Ile Pro Glu Ser Thr Arg Ile
    50                  55                  60

Arg Val Val Glu Ala Ala Gln Lys Leu Asn Tyr Arg Pro Asn Ala Gln
65                  70                  75                  80

Ala Arg Ala Leu Arg Lys Ser Arg Thr Asp Thr Ile Gly Val Ile Ile
                85                  90                  95

Pro Asn Ile Glu Asn Pro Tyr Phe Ser Ser Leu Ala Ala Ser Ile Gln
            100                 105                 110

Lys Ala Ala Arg Glu Ala Gly Val Ser Thr Ile Leu Ser Asn Ser Glu
        115                 120                 125

Glu Asn Pro Glu Leu Leu Gly Gln Thr Leu Ala Ile Met Asp Asp Gln
    130                 135                 140

Arg Leu Asp Gly Ile Ile Val Val Pro His Ile Gln Ser Glu Glu Gln
145                 150                 155                 160

Val Thr Asp Leu Val Asn Arg Gly Val Pro Val Val Leu Ala Asp Arg
                165                 170                 175

Ser Phe Val Asn Ser Ser Ile Pro Ser Val Thr Ser Asp Pro Val Pro
            180                 185                 190

Gly Met Thr Glu Ala Val Asp Leu Leu Leu Ala Asp Val Gln Leu
        195                 200                 205

Gly Tyr Leu Ala Gly Pro Gln Asp Thr Ser Thr Gly Gln Leu Arg Leu
    210                 215                 220

Asn Thr Phe Glu Arg Leu Cys Val Asp Arg Gly Ile Val Gly Ala Ser
225                 230                 235                 240

Val Tyr Tyr Gly Gly Tyr Arg Gln Glu Ser Gly Tyr Asp Gly Ile Lys
                245                 250                 255

Val Leu Ile Lys Gln Gly Ala Asn Ala Ile Ile Ala Gly Asp Ser Met

-continued

```
                260                 265                 270
Met Thr Ile Gly Ala Leu Leu Ala Leu His Glu Met Asn Leu Lys Ile
            275                 280                 285

Gly Glu Asp Val Gln Leu Ile Gly Phe Asp Asn Asn Pro Ile Phe Arg
            290                 295                 300

Leu Gln Asn Pro Pro Leu Ser Ile Ile Asp Gln His Val Gln Glu Ile
305                 310                 315                 320

Gly Lys Arg Ala Phe Glu Ile Leu Gln Lys Leu Ile Asn Gly Asp Thr
                325                 330                 335

Ala Gln Lys Ser Val Val Ile Pro Thr Gln Leu Ser Ile Asn Gly Ser
            340                 345                 350

Thr Ala Val Ser Gln Lys Ala Ala Lys Ala Ala Lys Ala Ala Gln
            355                 360                 365

Lys Ala Ala Lys Ala Ala Gln Asn Thr Gln His Glu Val Ser Leu
    370                 375                 380

Asp Gly Glu Leu
385

<210> SEQ ID NO 3
<211> LENGTH: 20
<212> TYPE: DNA
<213> ORGANISM: Corynebacterium glutamicum
<220> FEATURE:
<223> OTHER INFORMATION: Primer ccpA1intA

<400> SEQUENCE: 3
agagctgctt ggtcagactt                                          20

<210> SEQ ID NO 4
<211> LENGTH: 20
<212> TYPE: DNA
<213> ORGANISM: Corynebacterium glutamicum
<220> FEATURE:
<223> OTHER INFORMATION: Primer ccpA1intB

<400> SEQUENCE: 4
atccagattc ttggcggtag                                          20
```

US 7,101,690 B2

ATTENUATED CCPA1 MODIFIED BACTERIAL CELL AND ITS USE FOR THE PREPARATION OF L-AMINO ACIDS

CROSS-REFERENCE TO RELATED APPLICATIONS

The present application is a continuation application of U.S. application Ser. No. 09/938,540 filed Aug. 27, 2001, now U.S. Pat. No. 6,838,267, and claims the benefit of U.S. application Ser. No. 60/279,413 filed Mar. 29, 2001.

BACKGROUND OF THE INVENTION

1. Field of the Invention

The present invention provides nucleotide sequences from Coryneform bacteria which code for the ccpA1 gene and a process for the fermentative preparation of amino acids, in particular L-lysine, by attenuation of the ccpA1 gene. The ccpA1 gene codes for the ccpA1 protein, which is a catabolite control protein A.

2. Description of the Background

L-Amino acids, in particular L-lysine, are widely used, for example in human medicine, in the pharmaceuticals industry, in the foodstuffs industry and, very particularly, in animal nutrition.

It is known that amino acids may be prepared by fermentation from strains of Coryneform bacteria, in particular, *Corynebacterium glutamicum*. Due to the importance of L-amino acids, efforts are constantly made to improve preparatory processes therefor. Improvements can relate to fermentation measures, such as, for example, stirring and supply of oxygen, or the composition of the nutrient media, such as, for example, sugar concentration during the fermentation, or product work up by, for example, ion exchange chromatography, or the intrinsic output properties of the microorganism itself.

Methods of mutagenesis, selection and mutant selection are used to improve the output properties of these microorganisms. Strains which are resistant to antimetabolites or which are auxotrophic for metabolites of regulatory importance and which produce amino acids are obtained in this manner.

Methods using recombinant DNA techniques have also been employed for some years for improving *Corynebacterium* strains which produce L-amino acid. However, a need still exists for improved fermentation procedures for preparing amino acids, in particular L-lysine.

SUMMARY OF THE INVENTION

Accordingly, it is an object of the present invention to provide an improved fermentation process for producing amino acids, and in particular, L-lysine.

DETAILED DESCRIPTION OF THE PREFERRED EMBODIMENTS

At the outset, it is noted that where L-amino acids or amino acids are mentioned hereinafter, these terms will be understood to mean one or more amino acids, including their salts, which are L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and/or L-arginine.

Further, where L-lysine or lysine are mentioned hereinafter, this also means the salts, such as e.g. lysine monohydrochloride or lysine sulfate.

The present invention provides an isolated polynucleotide from Coryneform bacteria, containing a polynucleotide sequence which codes for the ccpA1 gene, chosen from:

a) polynucleotide which is identical to the extent of at least 70% to a polynucleotide which codes for a polypeptide which contains the amino acid sequence of SEQ ID No. 2, b) polynucleotide which codes for a polypeptide which contains an amino acid sequence which is identical to the extent of at least 70% to the amino acid sequence of SEQ ID No. 2, c) polynucleotide which is complementary to the polynucleotides of a) or b), and d) polynucleotide containing at least 15 successive nucleotides of the polynucleotide sequence of a), b) or c), the polypeptide preferably having the activity of the catabolite control protein CcpA1.

The present invention also provides the abovementioned polynucleotide, this preferably being a DNA which is capable of replication, containing:

(i) the nucleotide sequence shown in SEQ ID No.1, or (ii) at least one sequence which corresponds to sequence (i) within the range of the degeneration of the genetic code, or (iii) at least one sequence which hybridizes with the sequences complementary to sequences (i) or (ii), and optionally (iv) sense mutations of neutral function in (i).

The present invention also provides:

a DNA which is capable of replication and contains the nucleotide sequence as shown in SEQ ID No.1;

a polynucleotide which codes for a polypeptide which contains the amino acid sequence as shown in SEQ ID No. 2;

a vector containing parts of the polynucleotide according to the invention, but at least 15 successive nucleotides of the sequence claimed;

and Coryneform bacteria in which the ccpA1 gene is attenuated, in particular, by an insertion or deletion.

The present invention also provides polynucleotides which substantially contain a polynucleotide sequence, which are obtainable by screening by means of hybridization of a corresponding gene library of a Coryneform bacterium, which contains the complete gene or parts thereof, with a probe which contains the sequence of the polynucleotide according to the present invention according to SEQ ID No.1, or a fragment thereof, and isolation of the polynucleotide sequence mentioned.

Polynucleotide sequences according to the present invention are suitable as hybridization probes for RNA, cDNA and DNA, in order to isolate, in the full length, nucleic acids or polynucleotides or genes which code for the ccpA1 protein or to isolate those nucleic acids or polynucleotides or genes which have a high similarity with the sequence of the ccpA1 gene.

Polynucleotide sequences according to the present invention are furthermore suitable as primers with the aid of which DNA of genes which code for the ccpA1 protein can be prepared with the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

"Isolated" means separated out of its natural environment, and preferably purified.

"Polynucleotide" in general relates to polyribonucleotides and polydeoxyribonucleotides, it being possible for these to be non-modified RNA or DNA or modified RNA or DNA.

The polynucleotides according to the present invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which contain two or more amino acids bonded via peptide bonds.

The polypeptides according to the present invention include a polypeptide according to SEQ ID No. 2, in particular those with the biological activity of the ccpA1 protein, and also those which are at least 70%, preferably at least 80% and in particular at least 90% to 95% identical to the polypeptide according to SEQ ID No. 2 and have the activity mentioned.

The present invention moreover provides a process for the fermentative preparation of amino acids, in particular L-lysine, using coryneform bacteria which in particular already produce amino acids, and in which the nucleotide sequences which code for the ccpA1 gene are attenuated, in particular eliminated or expressed at a low level.

The term "attenuation" in this connection means or refers to the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

The term "enhancement" in this connection means or refers to the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

The microorganisms which the present invention provides can prepare amino acids, in particular L-lysine, from glucose, sucrose, lactose, fructose, maltose, molasses, starch, cellulose or from glycerol and ethanol. They can be representatives of Coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Exemplary strains of the genus *Corynebacterium*, in particular of the species *Corynebacterium glutamicum* (*C. glutamicum*), are, in particular, the known wild-type strains:
*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 or L-amino acid-producing mutants or strains prepared therefrom, such as, for example, the L-lysine-producing strains:
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM 5715 and
*Corynebacterium glutamicum* DSM 12866

Surprisingly, the present inventors have succeeded in isolating the new ccpA1 gene of *C. glutamicum* which codes for the ccpA1 protein, which is a catabolite control protein A.

To isolate the ccpA1 gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Genes and Clones, An Introduction to Genetic Engineering) (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börmann et al. (Molecular Microbiology 6(3), 317–326)) (1992)) in turn describe a gene library of *C. glutamicum* ATCC13032 using the cosmid pHC79 (Hohn and Collins, 1980, Gene 11, 291–298).

To prepare a gene library of *C. glutamicum* in *E. coli* it is also possible to use plasmids such as pBR322 (Bolivar, 1979, Life Sciences, 25, 807–818) or pUC9 (Vieira et al., 1982, Gene, 19:259–268). Suitable hosts are, in particular, those *E. coli* strains which are restriction- and recombination-defective, such as, for example, the strain DH5α (Jeffrey H. Miller: "A Short Course in Bacterial Genetics, A Laboratory Manual and Handbook for *Escherichia coli* and Related Bacteria", Cold Spring Harbour Laboratory Press, 1992).

The long DNA fragments cloned with the aid of cosmids or other-vectors can then be subcloned in turn into the usual vectors suitable for DNA sequencing.

Methods of DNA sequencing are described, inter alia, by Sanger et al. (Proceedings of the National Academy of Sciences of the United States of America USA, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the ccpA1 gene and which, as SEQ ID No. 1, is a constituent of the present invention has been found in this manner. The amino acid sequence of the corresponding protein has furthermore been derived from the present DNA sequence by the methods described above. The resulting amino acid sequence of the ccpA1 gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

Finally, DNA sequences which are prepared by the polymerase chain reaction (PCR) using primers which result from SEQ ID No. 1 are a constituent of the invention. Such. oligonucleotides typically have a length of at least 15 nucleotides.

Instructions for identifying DNA sequences by means of hybridization can be found, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and subsequently 0.5×SSC (The DIG System User's Guide for Filter Hybridisation, Boehringer Mannheim, Mannheim, Germany, 1995) a temperature of approx. 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

In accordance with the present invention, it has been surprisingly found that coryneform bacteria produce amino acids, in particular L-lysine, in an improved manner after attenuation of the ccpA1 gene.

To achieve an attenuation, either the expression of the ccpA1 gene or the catalytic properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998)), in Jensen and Hammer (Biotechnology and Bioengineering 58: 191 (1998)), in Patek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik (Molecular Genetics)", 6th edition, Georg Thieme Verlag, Stuttgart, Germany, 1995) or that by Winnacker ("Gene und Klone (Genes and Clones)", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms [Threonine dehydratase from *Corynebacterium glutamicum*: Cancelling the allosteric regulation and structure of the enzyme]", Reports from the Jülich Research Centre, Jül-2906, ISSN09442952, Jülich, Germany, 1994). Summarizing descriptions can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik (Molecular Genetics)", 6th edition, Georg Thieme Verlag, Stuttgart, Germany, 1995), that by Winnacker ("Gene und Klone (Genes and Clones)", VCH Verlagsgesellschaft, Weinheim, Germany, 1990) or that by Hagemann ("Allgemeine Genetik (General Genetics)", Gustav Fischer Verlag, Stuttgart, 1986).

A common method of mutating genes of *C. glutamicum* is the method of "gene disruption" and "gene replacement" described by Schwarzer and Puhler (Bio/Technology 9, 84–87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, The Netherlands; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of C. glutamicum.

In the method of "gene replacement", a mutation, such as e.g. a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al.(Microbiology 144, 915–927 (1998)) to eliminate the pyc gene of *C. glutamicum* by a deletion.

A deletion, insertion or a base exchange can be incorporated into the ccpA1 gene in this manner.

In addition, it may be advantageous for the production of L-amino acids, in particular L-lysine, to enhance, in particular to over-express, one or more enzymes of the particular biosynthesis pathway, of glycolysis, of anaplerosis, of the citric acid cycle, of the pentose phosphate cycle or of amino acid export and optionally regulatory proteins, in addition to attenuation of the ccpA1 gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

Thus, for example, for the preparation of L-lysine, at the same time one or more of the genes chosen from the group consisting of the dapA gene which codes for dihydrodipicolinate synthase (EP-B 0 197 335), the eno gene which codes for enolase (DE: 19947791.4), the zwf gene which codes for the zwf gene product (JP-A-09224661), at the same time the dapD gene which codes for tetradihydrodipicolinate succinylase (Wehrmann et al., Journal of Bacteriology 180, 3159–3165 (1998)), at the same time the dapE gene which codes for succinyl diaminopimelate desuccinylase (Wehrmann et al., Journal of Bacteriology 177: 5991–5993 (1995)), at the same time the gap gene which codes for glyceraldehyde 3-phosphate dehydrogenase (Eikmanns (1992). Journal of Bacteriology 174:6076–6086), the pyc gene which codes for pyruvate carboxylase (Peters-Wendisch et al. (Microbiology 144, 915–927 (1998))

at the same time the mqo gene which codes for malate: quinone oxidoreductase (Molenaar et al., European Journal of Biochemistry 254, 395–403 (1998)), the lysC gene which codes for a feed back resistant aspartate kinase (Kalinowski et al. (1990), Molecular and General Genetics 224, 317–324; Accession No.P26512; EP-B-0387527; EP-A-0699759; WO 00/63388), the zwa1 gene which codes for the Zwa1 protein (DE: 19959328.0, DSM 13115), the lysE gene which codes for lysine export (DE-A-19548222)

can be enhanced, in particular over-expressed.

It may furthermore be advantageous for the production of amino acids, in particular L-lysine, in addition to the attenuation of the ccpA1 gene, at the same time for one or more of the genes chosen from the group consisting of the pck gene which codes for phosphoenol pyruvate carboxykinase (DE 199 50409.1, DSM 13047), the pgi gene which codes for glucose 6-phosphate isomerase (U.S. Ser. No. 09/396,478, DSM 12969), the zwa2 gene which codes for the Zwa2 protein (DE: 19959327.2, DSM 13113), the poxB gene which codes for pyruvate oxidase DE: 19951975.7, DSM 13114)

to be attenuated.

In addition to attenuation of the ccpA1 gene it may furthermore be advantageous for the production of amino acids, in particular L-lysine, to eliminate undesirable side reactions, (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids, in particular L-lysine. A summary of known culture methods is described in the textbook by Chmiel (Bioprozesstechnik 1. Einführung in die Bioverfahrenstechnik (Bioprocess Technology 1. Introduction to Bioprocess Technology (Gustav Fischer Verlag, Stuttgart, 1991)) or in the textbook by Storhas (Bioreaktoren und periphere Einrichtungen (Bioreactors and Peripheral Equipment) (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivatization, or it can be carried out by reversed phase HPLC, for example as described by Lindroth et al. (Analytical Chemistry (1979) 51: 1167–1174).

The process according to the invention is used for the fermentative preparation of amino acids, in particular L-lysine.

The following microorganism was deposited on 22.08.2000 as a pure culture at the Deutsche Sammlung für Mikroorganismen und Zellkulturen (DSMZ=German Collection of Microorganisms and Cell Cultures, Braunschweig, Germany) in accordance with the Budapest Treaty:

Escherichia coli strain Top10F/pCR2.1ccpA1int DSM 13673.

The present invention is explained in more detail in the following with the aid of embodiment examples.

The isolation of plasmid DNA from Escherichia coli and all techniques of restriction, Klenow and alkaline phosphatase treatment were carried out by the method of Sambrook et al. (Molecular Cloning. A Laboratory Manual, 1989, Cold Spring Harbour Laboratory Press, Cold Spring Harbor, N.Y., USA). Methods for transformation of Escherichia coli are also described in this handbook.

The composition of the usual nutrient media, such as LB or TY medium, can also be found in the handbook by Sambrook et al.

The present invention will now be further illustrated by reference to certain Examples which are provided solely for purposes of illustration and are not intended to be limitative.

EXAMPLE 1

Preparation of a Genomic Cosmid Gene Library from C. glutamicum ATCC 13032

Chromosomal DNA from C. glutamicum ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the E. coli strain NM554 (Raleigh et al. 1988, Nucleic Acid Res. 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190)+100 µg/ml ampicillin. After incubation overnight at 37° C., recombinant individual clones were selected.

EXAMPLE 2

Isolation and Sequencing of the ccpA1 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the E. coli strain DH5αMCR (Grant, 1990, Proceedings of the National Academy of Sciences, U.S.A., 87:4645–4649) and plated out on LB agar (Lennox, 1955, Virology, 1:190) with 50 µg/ml zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR drhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No.

A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analyses were prepared with the XNIP program (Staden, 1986, Nucleic Acids Research, 14:217–231). Further analyses were carried out with the "BLAST search program" (Altschul et al., 1997, Nucleic Acids Research, 25:33893402) against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 1167 bp, which was called the ccpA1 gene. The ccpA1 gene codes for a polypeptide of 388 amino acids.

EXAMPLE 3

Preparation of an integration vector for integration mutagenesis of the ccpA1 gene From the strain ATCC 13032, chromosomal DNA was isolated by the method of Eikmanns et al. (Microbiology 140: 1817–1828 (1994)). On the basis of the sequence of the ccpA1 gene known for C. glutamicum from example 2, the following oligonucleotides were chosen for the polymerase chain reaction (see SEQ ID No. 3 and SEQ ID No. 4):

```
ccpA1intA:
5'AGA GCT GCT TGG TCA GAC TT 3' ccpA1intB:
5'ATC CAG ATT CTT GGC GGT AG 3'
```

The primers shown were synthesized by MWG Biotech (Ebersberg, Germany) and the PCR reaction was carried out by the standard PCR method of Innis et al. (PCR protocols. A guide to methods and applications, 1990, Academic Press) with Pwo-Polymerase from Boehringer. With the aid of the polymerase chain reaction, an internal fragment of the ccpA1 gene 362 bp in size was isolated.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991), Bio/Technology 9:657–663).

The E. coli strain TOP10F was then transformed with the ligation batch (Hanahan, In: DNA cloning. A practical approach. Vol. I, TOP 10F, IRL-Press, Oxford, Washington D.C., USA 1985). Selection for plasmid-carrying cells was made by plating out the transformation batch on LB agar (Sambrook et al., Molecular Cloning: A Laboratory Manual. $2^{nd}$ Ed., Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1ccpA1int.

EXAMPLE 4

Integration mutagenesis of the ccpA1 gene in the lysine Producer DSM 5715

The vector pCR2.1ccpA1int mentioned in example 3 was electroporated by the electroporation method of Tauch et al. (FEMS Microbiological Letters, 123:343–347 (1994)) in C. glutamicum DSM 5715. The strain DSM 5715 is an AEC-resistant lysine producer. The vector pCR2.1ccpA1int cannot replicate independently in DSM 5715 and is retained in the cell only if it has integrated into the chromosome of DSM 5715. Selection of clones with pCR2.1ccpA1 int integrated into the chromosome was carried out by plating out the electroporation batch on LB agar (Sambrook et al., Molecular Cloning: A Laboratory Manual. $2^{nd}$ Ed., Cold Spring Harbor Laboratory Press, Cold Spring Harbor, N.Y.), which had been supplemented with 15 mg/l kanamycin.

For detection of the integration, the ccpA1int fragment was labelled with the Dig hybridization kit from Boehringer by the method of "The DIG System Users Guide for Filter Hybridization" of Boehringer Mannheim GmbH (Mannheim, Germany, 1993). Chromosomal DNA of a potential integrant was isolated by the method of Eikmanns et al. (Microbiology 140: 1817–1828 (1994)) and in each case cleaved with the restriction enzymes PstI, SacI and HindIII. The fragments formed were separated by agarose gel electrophoresis and hybridized at 68° C. with the Dig hybridization kit from Boehringer. The plasmid pCR2. lccpA1int mentioned in example 3 had been inserted into the chromosome of DSM 5715 within the chromosomal ccpA1 gene. The strain was called DSM 5715::pCR2.1ccpA1int.

EXAMPLE 5

Preparation of L-Lysine

The C. glutamicum strain DSM 5715::pCR2.1ccpA1int obtained in example 4 was cultured in a nutrient medium suitable for the production of L-lysine and the L-lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

|  | Medium Cg III |
| --- | --- |
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4

Kanamycin (25 mg/l) was added to this. The preculture was incubated for 24 hours at 33° C. at 240 rpm on a shaking machine. A main culture was seeded from this preculture such that the initial OD (660 nm) of the main culture was 0.1 OD. Medium MM was used for the main culture.

|  | Medium MM |
| --- | --- |
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4.7 H_2O$ | 1.0 g/l |
| $CaCl_2.2H_2O$ | 10 mg/l |
| $FeSO_4.7 H_2O$ | 10 mg/l |
| $MnSO_4.H_2O$ | 5.0 mg/l |
| Biotin (sterile-filtered) | 0.3 mg/l |
| Thiamine.HCl (sterile-filtered) | 0.2 mg/l |
| Leucine (sterile-filtered) | 0.1 g/l |
| $CaCO_3$ | 25 g/l |

The CSL, MOPS and the salt solution are brought to pH 7 with aqueous ammonia and autoclaved. The sterile substrate and vitamin solutions are then added, as well as the $CaCO_3$ autoclaved in the dry state.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of L-lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD (660 nm) | Lysine HCl g/l |
| --- | --- | --- |
| DSM 5715 | 7.5 | 13.01 |
| DSM 5715::pCR2.1ccpA1int | 7.7 | 14.24 |

BRIEF DESCRIPTION OF THE FIGURE

FIG. 1: Map of the plasmid pCR2.1ccpA1int.

The abbreviations and designations used have the following meaning.

| KmR: | Kanamycin resistance gene |
| --- | --- |
| EcoRI: | Cleavage site of the restriction enzyme EcoRI |
| HindIII: | cleavage site of the restriction enzyme HindIII |
| PstI: | Cleavage site of the restriction enzyme PstI |
| SacI: | Cleavage site of the restriction enzyme SacI |
| ccpA1int: | Internal fragment of the ccpA1 gene |
| ColE1 ori: | Replication origin of the plasmid ColE1 |

What is claimed is:

1. A modified bacterial cell comprising an attenuated polynucleotide encoding a protein with ccpA1 catabolite control activity, wherein the polynucleotide prior to being attenuated comprises SEQ ID NO: 1; a polynucleotide which is at least 95% identical to SEQ ID NO: 1 and which encodes a protein with ccpA1 catabolite control activity; a polynucleotide which encodes a protein comprising the amino acid sequence of SEQ ID NO:2; or a nucleotide sequence which hybridizes under stringent conditions to the complement of SEQ ID NO:1, wherein said stringent conditions comprise washing in 0.5×SSC at 68° C. and wherein the nucleotide sequence encodes a protein with ccpA1 catabolite control activity.

2. The modified bacterial cell of claim 1, which is a Corynebacterium cell or an Escherichia coli cell.

3. The modified bacterial cell of claim 2, which is a Corynebacterium cell.

4. The modified bacterial cell of claim 3, which is a Corynebacterium glutamicum cell.

5. The modified bacterial cell of claim 2, which is an Escherichia coli cell.

6. The modified bacterial cell of claim 1, wherein the polynucleotide encoding a protein with ccpA1 catabolite control activity in the bacterial cell prior to being attenuated comprises SEQ ID NO: 1.

7. The modified bacterial cell of claim 1, wherein the polynucleotide encoding a protein with ccpA1 catabolite control activity in the bacterial cell prior to being attenuated comprises a polynucleotide which is at least 95% identical to SEQ ID NO: 1 which encodes a protein with ccpA1 catabolite control activity.

8. The modified bacterial cell of claim 1, wherein the polynucleotide encoding a protein with ccpA1 catabolite control activity in the bacterial cell prior to being attenuated comprises a nucleotide sequence which hybridizes under stringent conditions to the complement of SEQ ID NO: 1, wherein said stringent conditions comprise washing in 0.5× SSC at 68° C.

9. A process for preparing L-amino acids, which comprises culturing the modified bacterial cell of claim 1 in a medium suitable for producing L-amino acids; and collecting the L-amino acids.

10. The process of claim 9, wherein the modified bacterial cell expresses a reduced level of the protein with ccpA1 catabolite control activity, compared to an unmodified bacterial cell.

11. The process of claim 9, wherein the modified bacterial cell expresses a protein having reduced catabolite control activity compared to a ccpA1 catabolite control protein encoded by the polynucleotide prior to being attenuated expressed in an unmodified bacterial cell.

12. The process of claim 9, wherein the modified bacterial cell further comprises one or more of polynucleotides whose expression is increased relative to an unmodified bacterial cell, wherein the one or more polynucleotides are selected from the group consisting of:
- a dapA polynucleotide which codes for a protein with dihydrodipicolinate synthase activity,
- a eno polynucleotide which codes for a protein with enolase activity,
- a zwf polynucleotide which codes for a protein with zwf activity,
- a pyc polynucleotide which codes for a protein with pyruvate carboxylase acitivity,
- a lysE polynucleotide which codes for a protein with lysine export activity,
- a dapD polynucleotide which codes for a protiein with tetradihydrodipicolinate succinylase acitivity,
- a dapE polynucleotide which codes for a protein with succinyl diamino-pimelate desuccinylase acitivity,
- a gap polynucleotide which codes for a protein with glyceraldehyde 3-phosphate dehydrogenase acitivity,
- a mqo polynucleotide which codes for a protein with malate:quinone oxidoreductase activity,
- a lysC polynucleotide which codes for a protein with feed back resistant aspartate kinase activity, and
- a zwal polynucleotide which codes for a protein with Zwal protein activity.

13. The process of claim 9, wherein the modified bacterial cell is a *Corynebacterium* cell.

14. The process of claim 9, wherein the modified bacterial cell is a *Corynebacterium glutamicum* cell.

15. The modified bacterial cell of claim 1, wherein the polynucleotide encoding a protein with ccpA1 catabolite control activity in the bacterial cell prior to being attenuated comprises a polynucleotide encoding a protein comprising the amino acid sequence of SEQ ID NO:2.

* * * * *